United States Patent [19]
Murakami et al.

[11] Patent Number: 5,929,053
[45] Date of Patent: Jul. 27, 1999

[54] PESTICIDAL COMPOSITION AND METHOD FOR CONTROLLING PESTS USING THE SAME

[75] Inventors: Miwa Murakami, Minoo; Masao Ogawa, Funabashi; Izumi Fujimoto, Minoo; Toshiro Ohtsubo, Sanda, all of Japan

[73] Assignee: Sumitomo Chemical Company, Limited, Osaka, Japan

[21] Appl. No.: 08/767,300

[22] Filed: Dec. 16, 1996

[30] Foreign Application Priority Data

Dec. 20, 1995 [JP] Japan ................................ 7-331747

[51] Int. Cl.$^6$ .......................... A01N 57/16; A01N 25/26; A01N 25/28
[52] U.S. Cl. ...................... 514/89; 514/951; 514/963; 514/972; 424/408; 424/409; 424/417; 424/419; 424/451; 424/457; 424/489; 424/497; 424/501; 424/DIG. 11
[58] Field of Search ...................... 424/408, 409, 424/419, DIG. 11, 417, 451, 457, 489, 497, 501; 514/89, 951, 963, 972

[56] References Cited

U.S. PATENT DOCUMENTS

| | | | |
|---|---|---|---|
| 3,959,464 | 5/1976 | DeSavigny | 514/131 |
| 4,285,720 | 8/1981 | Scher | 71/DIG. 1 |
| 4,670,250 | 6/1987 | Baker | 424/419 |
| 4,696,822 | 9/1987 | Matsumura et al. | 424/490 |
| 4,874,611 | 10/1989 | Wilson et al. | 424/410 |
| 4,889,719 | 12/1989 | Ohtsubo et al. | 424/408 |
| 4,900,551 | 2/1990 | Ohtsubo et al. | 424/408 |
| 5,063,059 | 11/1991 | Ohtsubo et al. | 424/408 |
| 5,225,278 | 7/1993 | Kielbania, Jr. et al. | 71/DIG. 1 |
| 5,306,499 | 4/1994 | Ohtsubo et al. | 424/405 |
| 5,407,609 | 4/1995 | Tice et al. | 264/46 |
| 5,552,149 | 9/1996 | Lebo, Jr. et al. | 424/408 |
| 5,705,174 | 1/1998 | Benoff et al. | 424/408 |

FOREIGN PATENT DOCUMENTS

| | | |
|---|---|---|
| 0368576 | 5/1990 | European Pat. Off. . |
| 2206492 | 1/1989 | United Kingdom . |
| 95-23506 | 9/1995 | WIPO . |

*Primary Examiner*—John Pak
*Attorney, Agent, or Firm*—Sughrue, Mion, Zinn, Macpeak & Seas, PLLC

[57] ABSTRACT

A pesticidal composition comprising microcapsules, each microencapsulating an organophosphorus compound having a melting point of at least 15° C., a proportion (A) of aromatic ring structure in microcapsule wall material being not more than 40% by weight, and a ratio of (A) to (average diameter/wall thickness) of the microcapsules being not less than 0, but not more than 0.8, causes less color change to applied area even if applied outdoors.

6 Claims, No Drawings

PESTICIDAL COMPOSITION AND METHOD FOR CONTROLLING PESTS USING THE SAME

BACKGROUND OF THE INVENTION

1) Field of the Invention

The present invention relates to a novel pesticidal composition which comprises microcapsules, each microencapsulating an organophosphorus compound.

2) Related Art

Pesticidal compositions comprising microcapsules, each microencapsulating an organophosphorus compound, for example, chlorpyrifos, have been so far used to control wood-injuring insects. However, when pesticides comprising microcapsules, each microencapsulating an organophosphorus compound which is solid at room temperature, for example, chlorpyrifos, etc. are used outdoors, color change is sometimes observable in pesticide-sprayed areas, such as woods, etc. and improvement has been desired.

SUMMARY OF THE INVENTION

As a result of extensive studies, the present inventors found a novel pesticidal composition free from the color change problem.

According to the present invention, there is provided a pesticidal composition comprising microcapsules, each microencapsulating an organophosphorus compound having a melting point of at least 15° C., a proportion (A) of aromatic ring structure in microcapsule wall material being not more than 40% by weight and a ratio of (A) to (average diameter/wall thickness) of the microcapsules being not less than 0, but not more than 0.8 (the present pesticidal composition will be hereinafter referred to as "the present composition").

DETAILED DESCRIPTION OF THE INVENTION

The organophosphorus compound for use in the present invention has a melting point of at least 15° C. and includes, for example, the following effective compounds for insecticides, bactericides, fungicides and herbicides:

(1) O,O-diethyl O-3,5,6-trichloro-2-pyridyl phosphorothioate (chlorpyrifos)

(2) O,O-dimethyl O-3,5,6-trichloro-2-pyridyl phosphorothioate (chlorpyrifos-methyl)

(3) O,O-diethyl O-quinoxalin-2-yl phosphorothioate (quinalphos)

(4) O-(1,6-dihydro-6-oxo-1-phenylpyridazin-3-yl) O,O-diethyl phosphorothioate (pyridaphenthion)

(5) O,O-dimethyl S-(N-methylcarbamoylmethyl) dithiophosphate (dimethoate)

(6) S-α-ethoxycarbonylbenzyl O,O-dimethyl phosphorodithioate (PAP)

(7) S-6-chloro-2,3-dihydro-2-oxobenzoxazol-3-ylmethyl O,O-diethyl phosphorodithioate (phosalone)

(8) S-2,3-dihydro-5-methoxy-2-oxo-1,3,4-thiadiazol-3-ylmethyl O,O-dimethyl phosphorodithioate (DMTP)

(9) 2-chloro-1-(2,4-dichlorophenyl) vinyl dimethyl phosphate (dimethylvinphos)

(10) dimethyl 2,2,2-trichloro-1-hydroxyethylphosphonate (trichlorfon)

(11) O-ethyl O-4-nitrophenyl phenylphosphonothioate (EPN)

(12) O-2,6-dichloro-p-tolyl O,O-dimethyl phosphorothioate (tolclofos-methyl)

(13) O-methyl O-2-nitro-p-tolyl isopropylphosphoroamidothioate (amiprofos-methyl)

Microcapsulating procedure for use in the preparation of the present composition includes a procedure capable of easily controlling microcapsulating reaction, for example, so far well known interfacial polymerization process, an in-situ process, etc., among which the interfacial polymerization process is preferable for preparing the present composition owing to a wide selection range for microcapsule wall materials.

In the present invention, the microcapsule wall material includes, for example, polyurethane, polyurea, polyamide, polyester, polycarbonate, polysulfonate, polysulfonamide, urea-formalin condensation products, melamine-urea condensation products, phenol-formalin condensation products, acrylic acid ester polymer, methacrylic acid ester polymer, vinyl acetate polymer, styrene polymer, divinylbenzene polymer, ethylene-dimethacrylate polymer, etc.

Polyurethane microcapsule walls can be formed, that is, microcapsulation can be attained, for example, by interfacial polymerization of polyvalent isocyanate compounds and polyhydric alcohol compounds; polyurea microcapsule walls by interfacial polymerization of polyvalent isocyanate compounds and polyvalent amine compounds or water; polyamide microcapsule walls by interfacial polymerization of polyvalent acid chloride compounds and polyvalent amine compounds; polyester microcapsule walls by interfacial polymerization of polyvalent acid chloride compounds and polyhydric alcohol compounds, and so on, as in known from T. Kondo et al: New microcapsulating technique and its application development and actual application examples (published by Management Development Center, Japan) etc.

In the present invention, it is necessary that a proportion (A) of aromatic ring structure in the microcapsule wall material is not more than 40% by weight and a ratio of (A) to (average diameter/wall thickness) of the microcapsules is not less than 0, but not more than 0.8, that is, $$(A) \leq 40 \text{ wt. \%, and}$$

$$0 \leq \frac{(A)}{\text{Average diameter} \Big/ \text{wall thickness of}} \leq 0.8$$
$$\phantom{0 \leq \frac{(A)}{\text{Average}}} \text{of microcapsules} \quad \text{microcapsules}$$

For example, the value A can be lowered, for example, by keeping a proportion of a microcapsule wall forming material having the aromatic ring structure such as phenylene diisocyanate or phenylenediamine lower when polyurea microcapsule walls, etc. are formed by the above-mentioned interfacial polymerization process, and consequently the above-mentioned ratio can be satisfied. Needless to say, the value A can be made zero by using a microcapsule wall forming material having no aromatic ring structure at all, and consequently the above-mentioned ratio can be satisfied.

In view of the foregoing requirements for the microcapsule wall forming materials, preferable polyvalent isocyanate compounds for use in the formation of polyurethane microcapsule walls or polyurea microcapsule walls include, for example, hexamethylene diisocyanate, adducts of hexamethylene diisocyanate and trimethylolpropane, biuret condensation products of three molecules of hexamethylene diisocyanate, adducts of tolylene diisocyanate and trimethylolpropane, isocyanurate condensation products of tolylene diisocyanate, isocyanurate condensation products of hexamethylene diisocyanate, isocyanurate condensation products of isophorone diisocyanate, isocyanate prepolymers each constituted of one isocyanurate moiety that consists of one isocyanate part of hexamethylene diisocyanate and two molecules of tolylene diisocyanate and of another isocyanurate moiety that consists of another isocyanate part of the same hexamethylene diisocyanate and two molecules of other hexamethylene diisocyanate, 4,4'-methylenebis (cyclohexyl isocyanate), trimethyl hexamethylene diisocyanate, etc.

Polyhydric alcohol compounds for use in the formation of polyurethane microcapsule walls or polyester microcapsule walls includes, for example, ethylene glycol, propyrene glycol, butanediol, hexanediol, diethylene glycol, triethylene glycol, dipropylene glycol, polyethylene glycol, polypropylene glycol, glycerine, resorcin, hydroquinone, trimethylol propane, 1,2,6-hexanetriol, etc.

Polyvalent amine compounds for use in the formation of polyurea microcapsule walls or polyamide microcapsule walls includes, for example, ethylenediamine, buthanediamine, hexamethylenediamine, phenylenediamine, toluylenediamine, diethylenetriamine, triethylenetetramine, tetraethylenepentamine, pentaetnylenehexamine, 1,3,6-triaminonaphthalene, piperazine, etc.

Polyvalent acid chloride compounds for use in the formation of polyamide microcapsule walls or polyester microcapsule walls includes, for example, sebacoyl dichloride, adipoyl dichloride, azelaoyl dichloride, terephtaloyl chloride, trimesoyl chloride, pimeloyl dichloride, dodecanedioyl dichloride, citroyl dichloride, etc.

According to one embodiment of the present invention, there is provided a composition comprising microcapsules, each microencapsulating chlorpyrifos, which is particularly suitable for controlling wood-injuring insects such as termites, lyctus powder-post beetles, etc.

When the present composition comprising microcapsules, each microencapsulating chlorpyrifos as an organophosphorus compound, is used to control wood-injuring insects, it is preferable from the view point of an increase in the wood-injuring insect control effect and storage stability of compositions to prepare microcapsules so as to make the average microcapsule diameter not more than 30 $\mu$m, a ratio (average diameter/wall thickness) of microcapsules not less than 30, but not more than 200, and a product of (average diameter× wall thickness) of microcapsules not more than 20 $\mu$m$^2$.

The average diameter of microcapsules can be measured, for example, by Coulter Counter, Model TA-II (produced by Coulter Electronics Inc.).

The wall thickness of microcapsules can be calculated according to the following formula:

$$\text{Wall thickness} = \frac{\text{Average diameter}}{6} \times \frac{\text{Weight of microcapsule wall material}}{\text{Weight of microencapsulated substance(s)}} \times \frac{\text{Average density of microencapsulated substance(s)}}{\text{Average density of microcapsule wall material}}$$

When the present composition comprising microcapsules, each microencapsulating chlorpyrifos, is used to control termites, an effective dose of the present composition is applied directly to termites, or to habitat of or paths of termites. An application dose of the composition is about 5 to about 50 g/m$^2$ in case of spraying onto soil or concreate surfaces under house floors, about 50 to about 5000 g/m$^3$ in case of soil barrier treatment by mixing with soil, or about 1 to about 5 g/m$^2$ in case of wood treatment by spraying to wood surfaces, in terms of the weight of chlorpyrifos.

When the present composition comprising microcapsules, each microencapsulating chlorpyrifos, is used to make insect-proof plywoods to control lyctus powder-post beetles (*Lyctus brunneus Stephens*), the present composition is mixed with an adhesive and veneers are pasted and bonded to one another with the resulting adhesive containing the present composition in an application amount of about 10 to about 1,000 g/m$^3$ of plywood in terms of the weight of chlorpyrifos, followed by pressing with heating, thereby making insect-proof plywoods. The adhesive for use in making the insect-proof plywoods includes, for example, a urea resin adhesive, a melamine-urea adhesive, a modified phenol resin adhesive, an alkaline phenol resin adhesive, etc.

The present composition comprising microcapsules, each microencapsulating chlorpyrifos, is effective not only for controlling the wood-injuring insects, but also for controlling nuisance injurious insects such as ants, camel crickets, millipedes, centipedes, sowbugs, pill bugs, etc. In this case, the present composition can be sprayed directly to the nuisance injurious insects or habitat or paths of nuisance injurious insects in an amount of about 1 to about 50 g/m$^2$ in terms of the weight of chlorpyrifos.

The present composition can be formulated into various forms such as suspension concentrate (SC), dusts (DP), wettable powders (WP), granules (GR), etc., among which the suspension concentrate is often used from the view point of easy preparation and good storage stability. The suspension concentrate can be prepared by adding, if necessary, a stabilizer such as a thickening agent, an anti-freezing agent, a preservative, a specific gravity-regulating agent, etc. to a slurry obtained by microcapsulation reaction based on the interfacial polymerization process.

The thickening agent includes, for example, substances which exhibit a thickening effect in water, such as natural polysaccharides (e.g. xanthane gum, rhamthan gum, locust bean gum, carrageenan, wellan gum, etc.), synthetic polymers (e.g. sodium polyacrylate, etc.), semi-synthetic polymers (e.g. carboxymethyl cellulose, etc.), fine powders of minerals (e.g. aluminum magnesium silicate, smectite, bentonite, hectorite, silica, etc.), alumina sol, etc. The amount of the thickening agent in the present composition is usually 0 to 10% by weight.

The anti-freezing agent includes, for example, ethylene glycol, propylene glycol, glycerine, etc. The amount of the anti-freezing agent in the present composition is usually 0 to 20% by weight.

The preservative includes, for example, those which are used in the ordinary pest-controlling agent preparations such as p-hydroxybenzoic acid esters, salicyclic derivatives, etc. The amount of the preservative in the present composition is usually 0 to 10% by weight.

The specific gravity-regulating agent includes, for example, water-soluble salts such as sodium sulfate, etc., water-soluble fertilizer such as urea, etc., and the like. The amount of the specific gravity-regulating agent in the present composition is usually 0 to 50% by weight.

The amount of the organophosphorus compound as an active ingredient in the present composition is usually 0.5 to 80% by weight, though it depends on the kind of active ingredient, type of formulation of the present composition, etc., and in case of suspension concentrate, it is usually 0.5 to 50% by weight.

EMBODIMENTS OF THE INVENTION

The present invention will be described in detail below, referring to Production Example, Comparative Example and Test Examples.

PRODUCTION EXAMPLE 1

1.41 parts by weight of SUMIDUR L-75 (trademark of adduct of tolylene diisocyanate and trimethylolpropane, made by Sumitomo-Bayer Urethane Co., Japan; molecular weight: 656; 3 benzene rings are contained as aromatic rings in the molecule) and 20 parts by weight of chlorpyrifos were mixed together with heating to obtain a homogeneous mixture. Then, the resulting mixture was immediately added to 150 parts by weight of an aqueous solution containing 8% by weight of polyvinyl alcohol and 6% by weight of ethylene glycol and stirred at room temperature by a T. K. AUTO-HOMOMIXER (trademark of a homogenizer made by Tokushukika Kogyo Co., Japan) to obtain a dispersion of microfine droplets. Then, the dispersion was gently stirred at 60° C. for 24 hours to obtain a slurry containing microcapsules, each microencapsulating chlorpyrifos with a polyurethane microcapsule wall. Then, 228.59 parts by weight of an aqueous solution containing 2 parts by weight of xanthane gum and 4 parts by weight of aluminum magnesium silicate was added to the resulting slurry to obtain the present composition containing 5% by weight of microencapsulated chlorpyrifos.

It was found that the resulting microcapsules had an average diameter of 13.9 $\mu$m, a wall thickness of 0.15 $\mu$m, an (average diameter/wall thickness) value of 93, and an (average diameter×wall thickness) value of 2.1 $\mu$m$^2$, and furthermore that the proportion (A) of aromatic ring structure in the microcapsule wall material was 28.8% by weight and the ratio of (A) to (average diameter/wall thickness) was 0.31.

Production example of a comparative composition for Test Example, which follows, is given below as Comparative Example.

COMPARATIVE EXAMPLE 1

0.95 part by weight of MILLIONATE MR-400 (trademark of polyethylene polyphenyl polyisocyanate made by Nihon Polyurethane Kogyo K. K., Japan; one benzene ring is contained as an aromatic ring per methylene phenyl isocyanate unit in the molecule) and 20 parts by weight of chlorpyrifos were mixed together with heating to obtain a homogeneous mixture, and then the mixture was immediately added to 150 parts by weight of an aqueous solution containing 8% by weight of polyvinyl alcohol and 6% by weight of ethylene glycol and stirred at room temperature by T. K. AUTOHOMOMIXER to obtain a dispersion of microfine droplets. Then, the dispersion was gently stirred at 60° C. for 24 hours to obtain a slurry containing microcapsules, each microencapsulating chlorpyrifos with a polyurethane microcapsule wall. Then, 229.05 parts by weight of an aqueous solution containing 2 parts by weight of xanthane gum and 4 parts by weight of aluminum magnesium silicate was added to the resulting slurry to obtain a comparative composition containing 5% by weight of encapsulated chlorpyrifos.

It was found that the resulting microcapsules had an average diameter of 8.3 $\mu$m, a wall thickness of 0.1 $\mu$m, an (average diameter/wall thickness) value of 83 and an (average diameter×wall thickness) value of 0.83 $\mu$m$^2$, and further that the proportion (A) of aromatic ring structure in the microcapsule wall material was 45.6% by weight and the ratio of (A) to (average diameter/wall thickness) was 0.55.

TEST EXAMPLE 1

0.8 g each of the compositions, obtained in Production Example 1 and Comparative Example 1 were applied to filter papers, respectively, air-dried, and exposed to sun light for 3 days. No color change was observed in case of the present composition of Production Example 1, whereas color change to yellow was clearly observed in case of the comparative composition of Comparative Example 1.

TEST EXAMPLE 2

A sufficient amount (about 6 ml) of an aqueous 0.25 wt. % dilute solution of the present composition of Production Example 1 was directly sprayed to ten workers of Formosan subterranean termites from a 60 cm-distant position and a 100% mortality was observed one day thereafter.

The present composition causes less color change to applied area even if applied outdoors.

What is claimed is:

1. A pesticidal composition, comprising microcapsules containing an organophosphorous compound selected from the group consisting of chlorpyrifos and chlorpyrifos-methyl, wherein the microcapsules have an average diameter of not more than 30 $\mu$m, the weight percent value of aromatic ring structure in the microcapsule wall material is not more than 40, and the ratio of the weight percent value of aromatic ring structure in the microcapsule wall material to (average diameter/wall thickness) of the microcapsules is greater than 0, but not more than 0.8.

2. A pesticidal composition according to claim 1, wherein the organophosphorus compound is chlorpyrifos.

3. A pesticidal composition according to claim 2, wherein the microcapsules have an (average diameter/wall thickness) value of not less than 30, but not more than 200 and an (average diameter×wall thickness) value of not more than 20 $\mu$m$^2$.

4. A method for controlling wood-injuring insects, which comprises applying an effective amount of the composition of claim 2 or 3 to wood-injuring insects, or habitat or paths of wood-injuring insects.

5. A method for controlling termites, which comprises applying an effective amount of the composition of claim 2 or 3 to termites or habitat or paths of termites.

6. A method for controlling nuisance insects selected from the group consisting of ants, camel crickets, millipedes, centipedes, sowbugs, and pill bugs, which comprises applying an effective amount of the composition of claim 2 to said nuisance insects or habitat or paths of said nuisance insects.

* * * * *